(12) United States Patent
Chen et al.

(10) Patent No.: US 11,143,619 B1
(45) Date of Patent: Oct. 12, 2021

(54) PHOTO-IONIZATION DEVICE WITH IMPROVED LINEARITY AND STABILITY

(71) Applicant: Nanova Environmental, Inc., Columbia, MO (US)

(72) Inventors: Biyan Chen, Columbia, MO (US); Haisheng Zheng, Columbia, MO (US); Jun Yin, Columbia, MO (US); Qiao Zhang, Columbia, MO (US)

(73) Assignee: Nanova Environmental, Inc., Columbia, MO (US)

( * ) Notice: Subject to any disclaimer, the term of this patent is extended or adjusted under 35 U.S.C. 154(b) by 0 days.

(21) Appl. No.: 17/228,287

(22) Filed: Apr. 12, 2021

(51) Int. Cl.
*G01N 27/64* (2006.01)
*G01N 33/00* (2006.01)
*G01N 27/626* (2021.01)
*G01N 21/27* (2006.01)
*G01N 27/62* (2021.01)
*G01N 27/407* (2006.01)
*G01N 30/64* (2006.01)

(52) U.S. Cl.
CPC ............. *G01N 27/64* (2013.01); *G01N 21/27* (2013.01); *G01N 27/4074* (2013.01); *G01N 27/62* (2013.01); *G01N 27/628* (2013.01); *G01N 33/0047* (2013.01); *G01N 2030/642* (2013.01); *G01N 2223/502* (2013.01)

(58) Field of Classification Search
CPC .... G01N 27/64; G01N 27/4074; G01N 27/62; G01N 27/628; G01N 21/27; G01N 33/0047; G01N 2030/642; G01N 2223/502
USPC ........................................................ 250/397
See application file for complete search history.

(56) References Cited

U.S. PATENT DOCUMENTS

| | | | |
|---|---|---|---|
| 2002/0003860 A1* | 1/2002 | Francke | H01J 47/008 378/98.8 |
| 2011/0133071 A1* | 6/2011 | Bashkirov | G01T 1/185 250/282 |

* cited by examiner

*Primary Examiner* — Kiet T Nguyen
(74) *Attorney, Agent, or Firm* — Finnegan, Henderson, Farabow, Garrett & Dunner, LLP

(57) ABSTRACT

A gas ionization chamber, includes a first electrode, a fence electrode disposed below the first electrode, a second electrode disposed below the fence electrode, a first dielectric layer disposed between the first electrode and the fence electrode, and a second dielectric layer disposed between the fence electrode and the second electrode. The first and second electrodes, and the first and second dielectric layers include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes, and wherein a diameter of at least one hole of the first set of aligned holes is less than or equal to about 0.5 millimeters.

20 Claims, 13 Drawing Sheets

100

110

PHOTO-IONIZATION DEVICE WITH IMPROVED LINEARITY AND STABILITY

TECHNICAL FIELD

The present disclosure relates to a system for detecting gases and more particularly, to photo-ionization detectors for detecting volatile gases.

BACKGROUND

Photo-ionization detectors (PIDs) are frequently used for detecting volatile gases such as volatile organic compounds (VOCs). In some cases, PIDs may not be configured to differentiate between different types of VOCs and may determine total VOCs (TVOCs). A typical PID includes a source of high-energy photons, an ionization chamber, and an ion detector. A typical high-energy light source is a gas discharge ultraviolet (UV) lamp which produces high-energy photons. The high-energy photons are directed into the ionization chamber and may interact with molecules having ionization potentials below the energies of the photons. Such interaction results in ionized molecules which are electrically detectable.

One of the limitations of typical PIDs is their unsatisfactory linearity, especially at a high concentration of volatile gases. For example, most commonly available PIDs deviate at higher concentrations. Due to a lack of linearity, PIDs require multiple calibrations for different concentration values. Even when multiple-point calibration is performed, the accuracy of PIDs may be inadequate for some values of volatile gas concentrations that are sufficiently different from calibration concentration values.

The disclosed photo-ionization device may address one or more of the problems set forth above and/or other problems in the prior art.

SUMMARY

Disclosed embodiments provide a photo-ionization device with improved linearity and stability for detecting volatile gases. The photo-ionization device includes a gas ionization chamber.

Consistent with a disclosed embodiment, a gas ionization chamber, includes a set of stacked elements. The set of stacked elements includes a first electrode, a fence electrode disposed below the first electrode, and a second electrode disposed below the fence electrode. Further, the set of stacked elements includes a first dielectric layer disposed between the first electrode and the fence electrode and a second dielectric layer disposed between the fence electrode and the second electrode, wherein at least the first electrode, the second electrode, the first dielectric layer, and the second dielectric layer include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes, and wherein a diameter of at least one hole of the first set of aligned holes is less than or equal to about 0.5 millimeters.

Consistent with another disclosed embodiment, a photo-ionization detector for testing gas, is provided. The photo-ionization detector includes a gas ionization chamber having a set of stacked elements. The set of stacked elements includes a first electrode, a fence electrode disposed below the first electrode, and a second electrode disposed below the fence electrode. Further, the set of stacked elements includes a first dielectric layer disposed between the first electrode and the fence electrode and a second dielectric layer disposed between the fence electrode and the second electrode, wherein at least the first electrode, the second electrode, the first dielectric layer, and the second dielectric layer include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes, and wherein a diameter of multiple holes of the first set of aligned holes is less than or equal to about 0.5 millimeters. Further, the gas ionization chamber includes a set of electrically conductive pins. The set of electrically conductive pins includes a first electrically conductive pin electrically connected to the first electrode, a second electrically conductive pin electrically connected to the fence electrode; and a third electrically conductive pin electrically connected to the second electrode, wherein the first, second, and third electrically conductive pins are arranged in a triangular pattern. Further, the photo-ionization detector includes an ionization light source positioned such that ionization light from the ionization light source is configured to pass through the plurality of the aligned holes for ionizing gas within the plurality of the aligned holes, and a circuit board electrically connected to both the ionization chamber and the ionization light source.

Consistent with another disclosed embodiment a photo-ionization detector for testing gas is provided. The photo-ionization detector includes a set of stacked elements. The set of stacked elements includes a first electrode, a fence electrode disposed below the first electrode, and a second electrode disposed below the fence electrode. The set of stacked elements further includes a first dielectric layer disposed between the first electrode and the fence electrode, and a second dielectric layer disposed between the fence electrode and the second electrode, wherein at least the first electrode, the second electrode, the first dielectric layer, and the second dielectric layer include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes, and wherein a diameter of each hole of the first set of aligned holes is less than or equal to about 0.5 millimeters and a diameter of each hole of the second set of aligned holes is equal and one of (a) less than or equal to about 0.5 millimeters or (b) greater than 0.5 millimeters. Further, the gas ionization chamber includes a first electrically conductive pin electrically connected to the first electrode, a second electrically conductive pin electrically connected to the fence electrode, and a third electrically conductive pin electrically connected to the second electrode, wherein the first, second, and third electrically conductive pins are arranged in a triangular pattern. Further, the set of stacked elements includes a fourth and fifth electrically conductive pins electrically connected to the fence electrode. The photo-ionization detector also includes an ionization light source positioned such that ionization light from the ionization light source is configured to pass through the plurality of the aligned holes for ionizing gas within the plurality of the aligned holes, a circuit board electrically connected with the stacked elements via the first, second, third, fourth, and fifth pins, and electrically connected with the ionization light source, and a metallic enclosure with a top cap having a plurality of openings, wherein the metallic enclosure houses the ionization chamber, the ionization light source, and the circuit board, and wherein the plurality of openings allow the testing gas flowing through the ionization chamber.

The foregoing general description and the following detailed description are exemplary and explanatory only and are not restrictive of the claims.

BRIEF DESCRIPTION OF THE DRAWINGS

The accompanying drawings are not necessarily to scale or exhaustive. Instead, the emphasis is generally placed upon illustrating the principles of the embodiments described herein. These drawings, which are incorporated in and constitute a part of this specification, illustrate several embodiments consistent with the disclosure, and, together with the detailed description, serve to explain the principles of the disclosure. In the drawings.

DETAILED DESCRIPTION

Reference will now be made in detail to exemplary embodiments, discussed with regard to the accompanying drawings. In some instances, the same reference numbers will be used throughout the drawings and the following description to refer to the same or like parts. Unless otherwise defined, technical and/or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting. In this disclosure, relative terms, such as, for example, about, substantially, etc., have a variation of 10% from the references term. For example, a diameter of about 1 mm may vary from 1 mm by 10%.

Figure 1A:
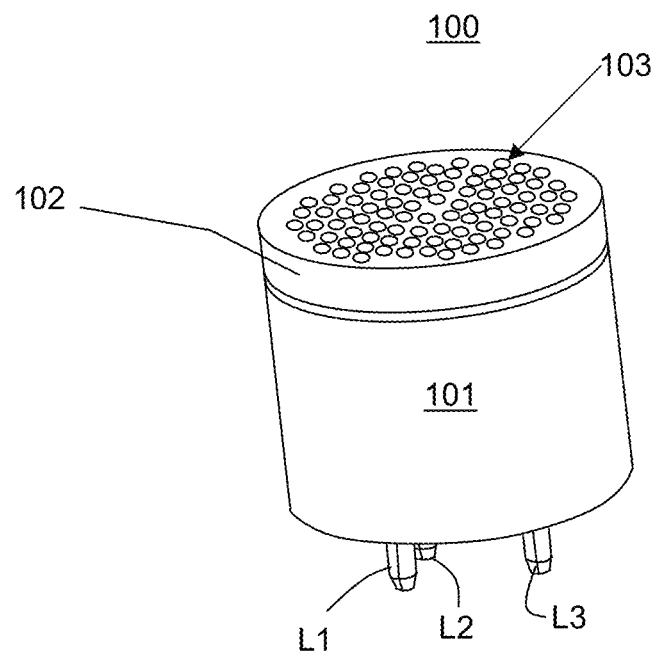
FIGS. 1A-1C show an illustrative photo-ionization detector, consistent with disclosed embodiments.
Figure 1B:
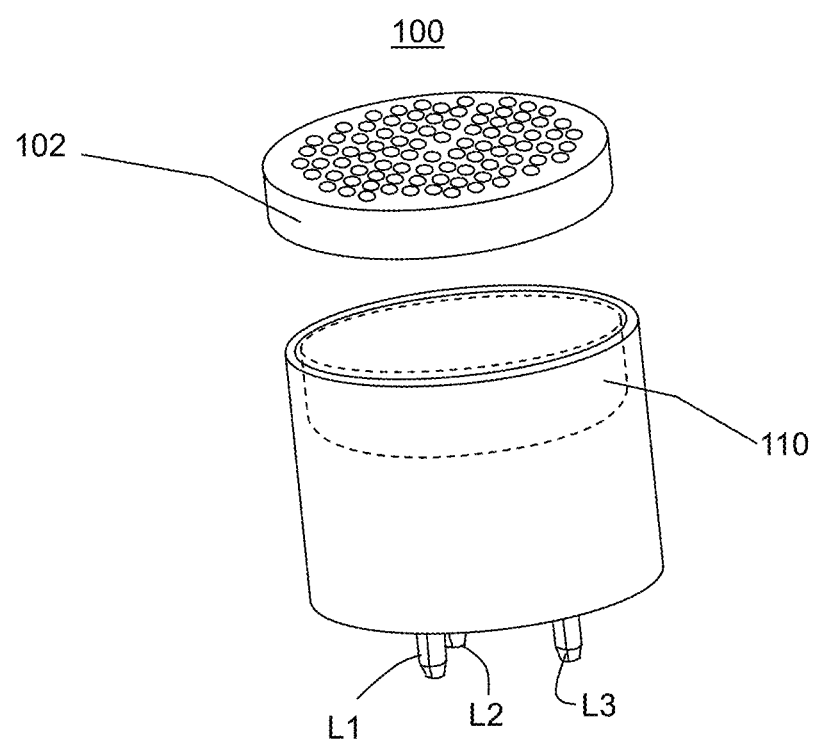
Figure 1C:
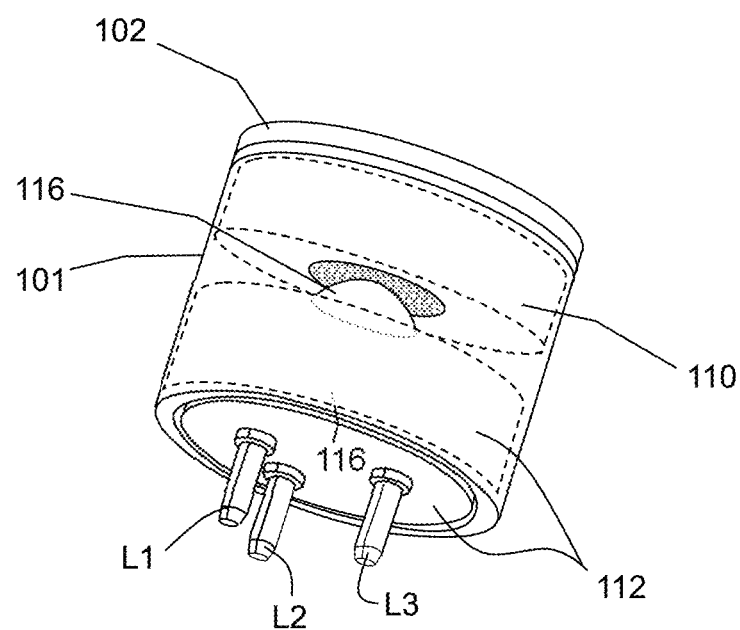

The disclosed embodiments relate to a device (herein, also referred to as a detector) that uses photo-ionization to detect a gas such as volatile organic compounds (VOCs). An example embodiment of detector 100 is shown in FIGS. 1A-1C. Detector 100 may include an enclosure 101, as shown in FIGS. 1A and 1B. Enclosure 101 may include a top cap 102, which may be removable, as shown in FIG. 1B. Top cap 102 includes openings 103 configured to allow gas (e.g., gas mixture containing VOCs) to enter enclosure 101. In an example embodiment, enclosure 101 comprises a conductive material (e.g., a metal such as aluminum, copper, steel, etc.).

In an example embodiment, enclosure 101 houses a gas ionization chamber 110, a printed circuit board (herein, also referred to as PCB) 112, and an ionization light source (herein, also referred as light source, radiation source, or ionization source) 116. Ionization chamber 110 is electronically connected to PCB 112. Light source 116 is placed underneath ionization chamber 110 and electronically connected to PCB 112 to produce light for ionization chamber 110. PCB 112 is further connected to a plurality of legs L1-L3, and some legs may be configured to provide power to the detector. While three legs L1-L3 are shown, more legs may be used for various electrical connections. In an example embodiment, enclosure 101 may be grounded (i.e., maintained at a ground potential level) by electrically connecting to PCB 112, which may be grounded. In an example embodiment, enclosure 101 may be connected to PCB 112 via electrically conductive paste.

Figure 2:
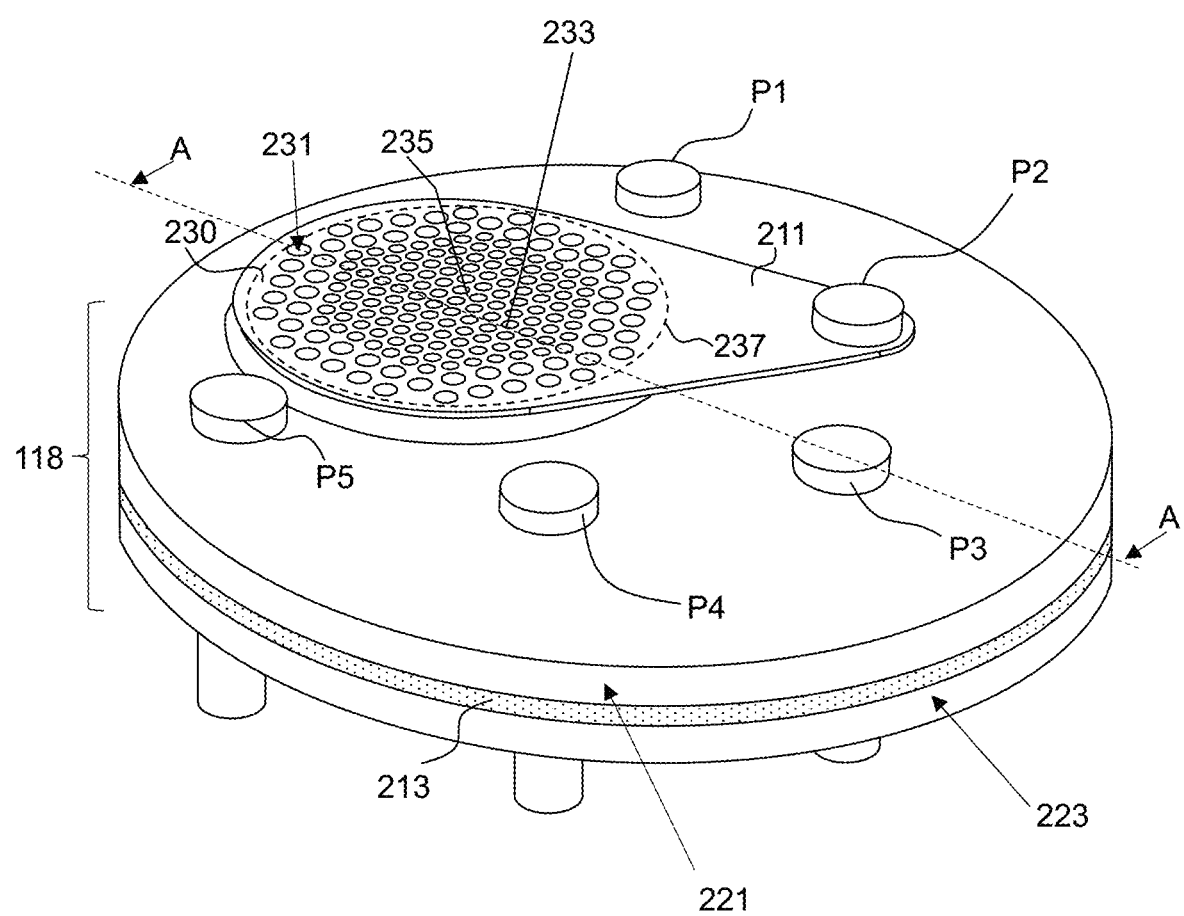
FIG. 2 is an example of a gas ionization chamber, consistent with disclosed embodiments.
Figure 3:
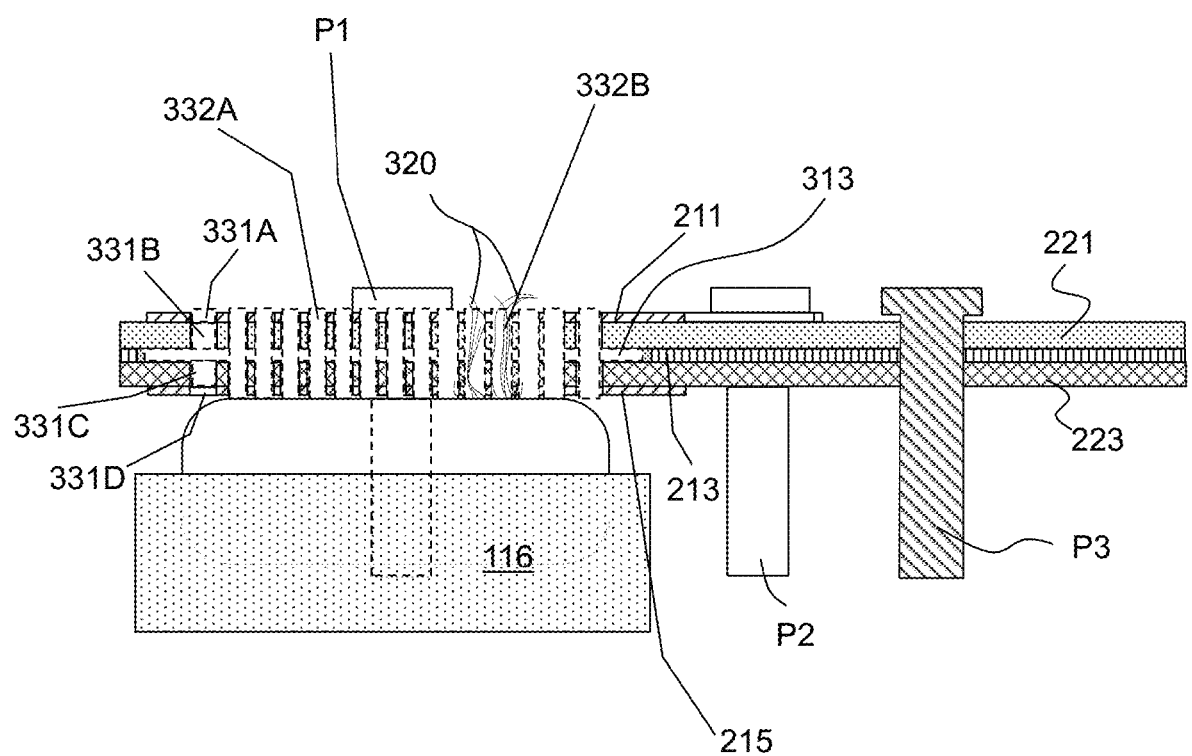
FIG. 3 is a cross-section of an example gas ionization chamber, consistent with disclosed embodiments.
Figure 4:
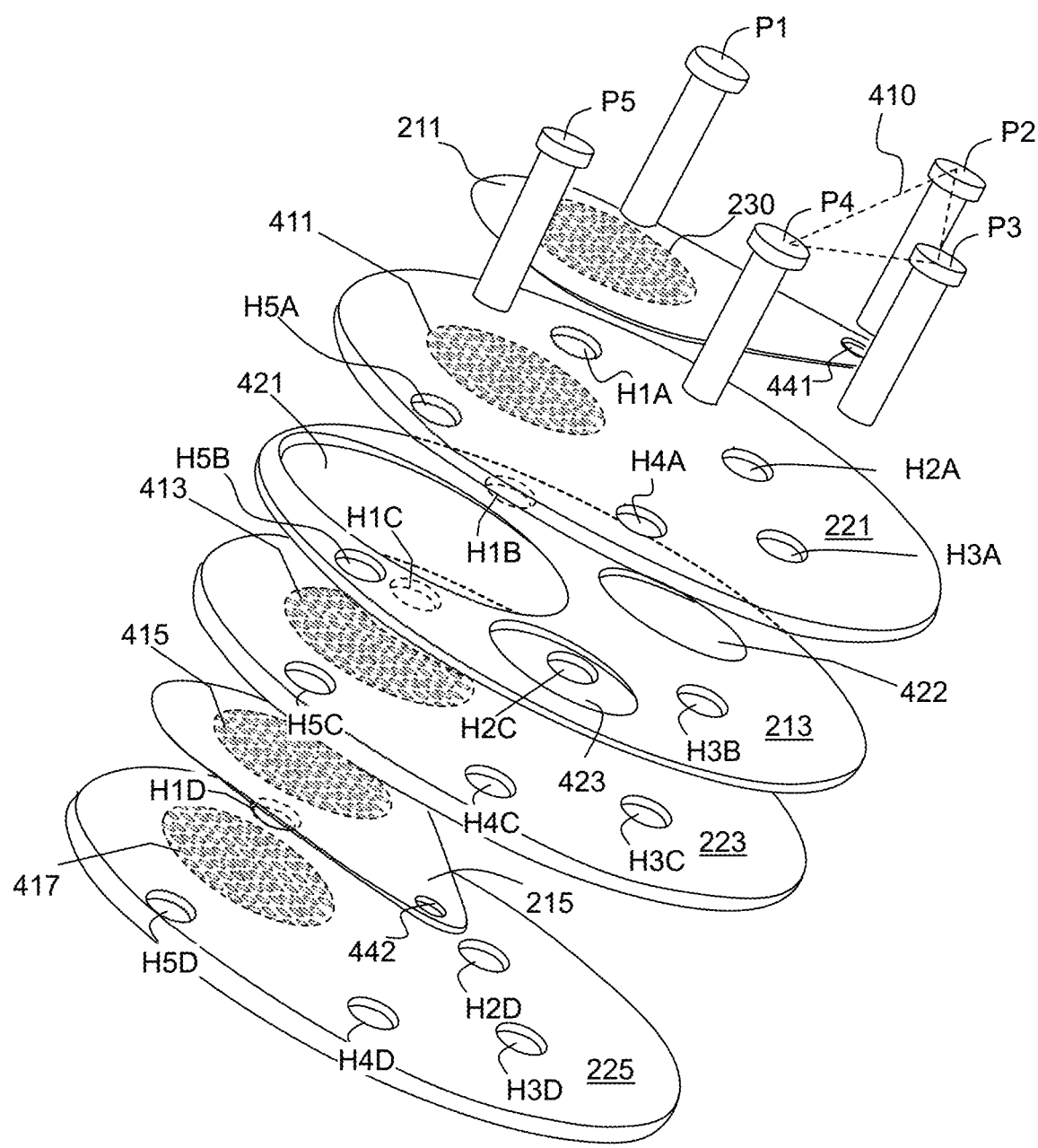
FIG. 4 is an exploded view of an example gas ionization chamber, consistent with disclosed embodiments.

Gas ionization chamber 110 is further shown in FIGS. 2-4. In an example embodiment, gas ionization chamber 110 may be removable/replaced from enclosure 101. For instance, chamber 110 may be a separate consumable component from detector 100. In various embodiments, as shown in FIG. 2, chamber 110 may include a set of stacked elements 118 and a plurality of pins, such as pins P1-P5, as shown in FIG. 2. In an example embodiment, set of stacked elements 118 includes a first electrode 211, a first dielectric layer 221, a fence electrode 213, a second dielectric layer 223, and a second electrode 215, as shown in FIG. 4. In some cases, set of stacked elements 118 includes a third dielectric layer 225, as shown in FIG. 4. Further, chamber 110 is configured to include pins P2-P4, each one connecting with respective electrodes 211, 213, and 215. Pins P2-P4 are placed in a triangular orientation, further described below. Additionally, chamber 110 may include one or more additional pins for additional structure support. The additional pins may be connected with fence electrode 213 and may not be connected to electrodes 211 and 215. In various embodiments, all pins may be connected to PCB 112.

As described above, detector 100 includes radiation source 116, as shown in FIG. 1C, positioned between gas ionization chamber 110 and PCB 112. In an example embodiment, radiation source 116 may be configured to be removable/replaced. In an example embodiment, detector 100 may be assembled by placing a PCB 112 in open enclosure 101, followed by inserting radiation source 116 and electrically connecting radiation source 116 to PCB 112. Subsequently, detector 100 may be assembled by inserting chamber 110, such that radiation source 116 is directly below chamber 110, as further described below. In various embodiments, when inserting chamber 110, pins (e.g., pins P1-P5) of chamber 110 are configured to be electrically connected to PCB 112. Assembly of detector 100 may be completed by closing enclosure 101 of detector 100 with top cap 102, as shown in FIGS. 1A and 1B.

In various embodiments, PCB 112 may power radiation source 116 and may connect to electrodes 211, 213, and 215 via corresponding pins P2-P4. PCB 112 may be connected to enclosure 101 via a conductive paste and may be grounded via one of the legs L1-L3.

FIG. 2 shows a three-dimensional view of gas ionization chamber 110. Chamber 110 may include a set of stacked elements 118 and a set of pins (P1-P5). In an example embodiment, a first element in the set of stacked elements is first electrode 211 (herein, also referred to as a top electrode 211), having a region 230 containing holes (e.g., holes 231 and 233) that penetrate through first electrode 211 (herein, also referred to as electrode 211). Region 230 may have a central point 235 and a peripheral boundary 237. In an example embodiment, when region 230 is generally circular, central point 235 is at about the center of the circular region. Similarly, when region 230 is a generally hexagonal region, central point 235 is a point at about the center of the generally hexagonal region, and for a generally rectangular region, central point 235 is at about the point where diagonals of the generally rectangular region intersect. For an elliptical region, central point 235 is at about a midpoint of both the major and minor axes of the elliptical region. For region 230 having other shapes, central point 235 may be a point at about a center of mass of region 230.

In various embodiments, first electrode 211 may be made of a conductive material such as metal. For example, first electrode 211 can be made from copper, aluminum, gold, silver, zinc, nickel, iron, steel, highly-doped semiconductor, combinations thereof, etc. First electrode 211 is electrically connected to a pin P2, which is configured to deliver a direct voltage to first electrode 211. The direct voltage may range from a few tens to a few hundred volts. In some embodiments, first electrode 211 may be positioned directly above first dielectric layer 221. For example, in some embodiments, first electrode 211 may be stacked atop first dielectric layer 221.

First dielectric layer 221 (herein, also referred to as dielectric layer 221 or layer 221) includes holes (not shown in FIG. 2, see FIG. 4) aligned with holes of first electrode 211. Such hole alignment results in channels penetrating or extending through, first electrode 211 and first dielectric layer 221. The sizes and shapes of the holes in first dielectric layer 221 are configured to be the same as the sizes and shapes of corresponding holes in first electrode 211. First dielectric layer 221 may be formed from any suitable insulating material. For example, first dielectric layer 221 may be formed from a suitable fluoropolymer such as, for example, polytetrafluoroethylene, ceramic, glass, non-conductive polymer, combinations thereof, etc. In one embodiment, first dielectric layer 221 may be formed from silicon nitride, silicon oxide, aluminum oxide, boron nitride, or any other suitable insulating material that may not chemically interact with an ionized gas in gas ionization chamber 110.

In an example embodiment, set of stacked elements 118 further includes fence electrode 213, second dielectric layer 223, and second electrode 215 (not shown in FIG. 2), as further described below. In some cases, set of stacked elements 118 includes third dielectric layer 225 (not shown in FIG. 2). Gas ionization chamber 110 may include several pins (e.g., pins P1-P5, as shown in FIG. 2). At least some pins P1-P5 may be conductive (e.g., pin P2 is configured to be conductive and connected to electrode 211) and configured to direct signals, etc., to and/or from gas ionization chamber 110.

FIG. 3 shows a cross-sectional view of gas ionization chamber 110 selected along a cut line A, as shown in FIG. 2. In some embodiments, chamber 110 includes set of stacked elements 118, with the first element being first electrode 211, which is followed by first dielectric layer 221. Adjacent to and directly below first dielectric layer 221 is fence electrode 213, which is followed by second dielectric layer 223. A second electrode 215 follows second dielectric layer 223 and is directly adjacent to second dielectric layer 223. In various embodiments, first electrode layer 211 includes holes such as a hole 331A, and first dielectric layer 221 includes holes (e.g., hole 331B) that are aligned underneath the holes of first electrode 211. In an example embodiment, holes of first dielectric layer 221 are of the same size and shape as corresponding holes of first electrode 211 that are aligned with holes of first dielectric layer 221. In some embodiments, fence electrode 213 includes a large opening 313, as shown in FIG. 3. Additionally, second dielectric layer 223 includes holes (e.g., hole 331C) that are aligned underneath the holes of first dielectric layer 221. In an example embodiment, holes of second dielectric layer 223 are of the same size and shape as corresponding holes of first electrode 211 and first dielectric layer 221 that are aligned with holes of second dielectric layer 223. Furthermore, second electrode 215 also includes holes (e.g., hole 331D) that are aligned with holes of second dielectric layer 223 and are of the same size and shape as corresponding holes of second dielectric layer 223. As shown in FIG. 3, aligned holes, such as holes 331A-331D, form channels (e.g., channels 332A and 332B) that extend through set of stacked elements 118, forming gas ionization chamber 110. When discussing aligned holes, such as holes 331A-331D, in relation to hole sizes, hole arrangement, or distribution of holes, it should be understood, unless specified otherwise, that holes are considered in the same lateral plane (e.g., holes in a plane of first electrode 211). When discussing aligned holes in relation to the flow of ionized gas from first electrode 211 to second electrode 215, such aligned holes are referred to as channels to further indicate that these holes extend through gas ionization chamber 110.

It should be noted that the configuration of chamber 110 discussed above is only exemplary, and many variations are possible. For example, in some embodiments, interfacial layers may be provided between one or more of the layers (e.g., between first electrode 211 and first dielectric layer 221, between first dielectric layer 221 and fence electrode 213, etc.) discussed above. Further, in some embodiments, one or more of the layers discussed above (e.g., first electrode 211, first dielectric layer 221, fence electrode 213, etc.) may include one or more layers that together act as one of the described layers. For example, in some embodiments, multiple (insulating) layers stacked one atop another function together as the first dielectric layer, etc.

During the operation of detector 100, a potential difference is applied between first electrode 211 and second electrode 215. In an example embodiment, electrode 211 may be connected to a cathode, and electrode 215 may be connected to an anode. For example, electrode 211 may be at a lower potential level than the ground potential, and electrode 215 may be at a higher potential level than the ground potential. A gas (e.g., a gas mixture contains various VOCs) may enter openings 103, shown in FIG. 1A, and penetrate channels (e.g., channel 332B) as indicated by flow lines 320. Within channel 332B, the gas may be ionized by light of ionization source 116, resulting in positively charged ions and negatively charged electrons. Positively charged gas ions may migrate towards first electrode 211, while electrons may migrate towards second electrode 215, resulting in a small current between first electrode 211 and second electrode 215 that is detectable by an amplifier.

Ionization source 116 may be any suitable ultraviolet lamp (UV lamp). In one embodiment, ionization source 116 is directly fixed on PCB 112. Ionization source 116 may transmit UV light in a wavelength range from about 100 nm to 210 nm. In some embodiments, multiple ionization sources may be used to provide selectivity for various VOCs. Ionization source 116 can be selected to provide UV lights with different energy levels, such as energies of 8.4 eV, 9.6 eV, 9.8 eV, 10 eV, 10.2 eV, 10.6 eV, or 11.7 eV.

A typical current due to ionized gas may be on the order of pico-amperes to microamperes. In order to achieve accurate measurement of the small current, a current amplifier is used to amplify the signal. In an example embodiment, PCB 112, as shown in FIG. 1B, includes at least one amplifying circuit, which amplifies the response signal generated by ion sensing electrodes to form amplified signals. The amplified signals are transmitted to a processor, which may be mounted on PCB 112. Any suitable current amplifier may be used, such as, for example, a trans-impedance amplifying circuit or a current-to-current amplifying circuit.

In some cases, PCB 112 may include a filtering circuit. The filtering circuit may reduce the measurement noise. The noise may be due to temperature variation, humidity interference, electromagnetic interference, capacitive coupling, inductive coupling, or other electrochemical interferences.

Further, a current due to ionized gas detected at the second electrode 215 may be amplified by the amplifier circuit connected to the second electrode 215. To further reduce the noise associated with current measurements, a fence electrode may also be attached to the ground and may help eliminate the leakage current that may be resulted due to the production of photoelectrons by ionized light or due to current along surfaces of electrodes and dielectrics due to humidity.

Figure 5:
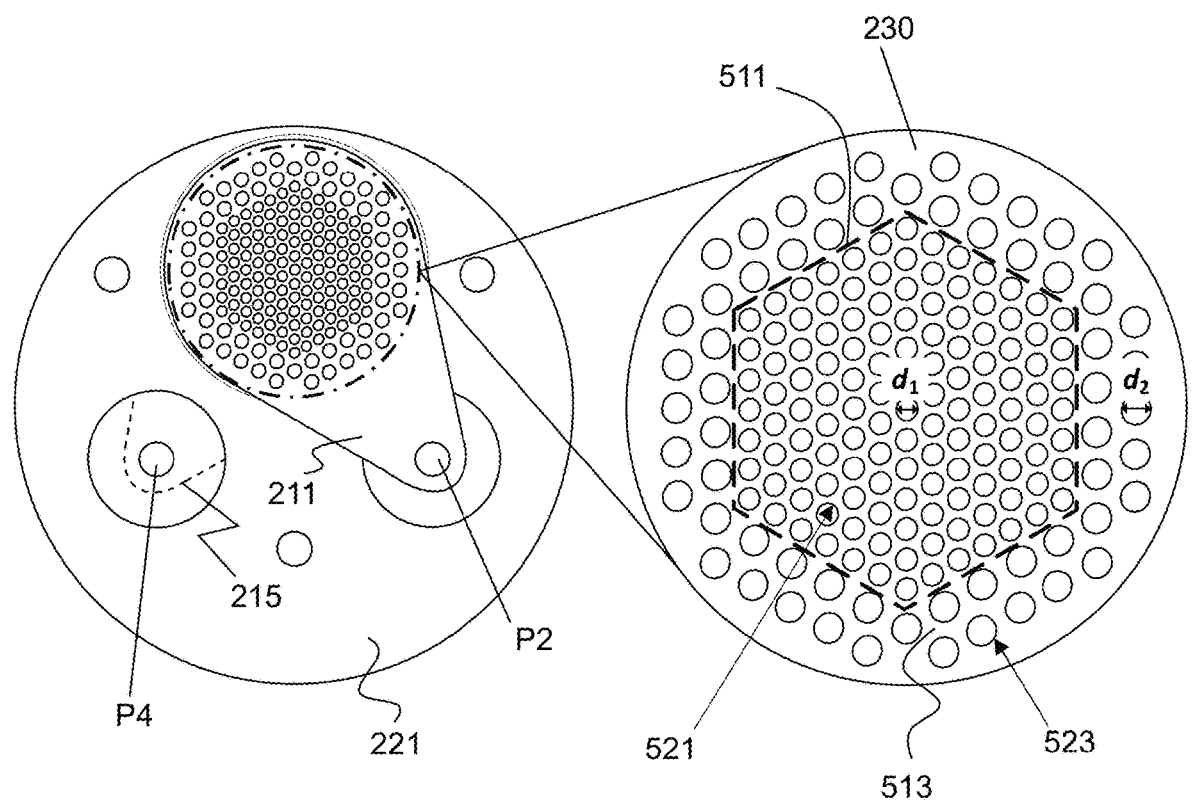
FIG. 5 is a top view of an example gas ionization chamber, consistent with disclosed embodiments.

FIG. 4 shows an exploded view of stack elements forming gas ionization chamber 110. In an example embodiment, first electrode 211 includes region 230 containing holes. In an example embodiment, region 230 may be substantially circular, hexagonal, rectangular, elliptical, etc. First electrode 211 may be of any suitable shape. In some cases, first electrode 211 may be of a circular shape or of a teardrop shape, as shown in FIGS. 2, 4, and 5. For example, the teardrop shape of first electrode 211 facilitates electrical connection of first electrode 211 to conductive pin P2 being sufficiently removed from region 230. Similarly, second electrode 215 may be of any suitable shape. In an example embodiment, second electrode 215 may also have a teardrop shape, as shown in FIG. 4. The teardrop shape of second electrode 215 facilitates electrical connection of second electrode 215 to conductive pin P4 being sufficiently removed from region 230.

In various embodiments, the shape of gas ionization chamber 110 may be circular, hexagonal, rectangular, etc. In an example embodiment, elements of gas ionization chamber 110 (e.g., electrodes 211, 213, 215, and dialectic layers 221, 223, and 225) may have a lateral area that is about the size of PCB 112 in order to maximize region 230. In an example embodiment, region 230 may be smaller than the lateral area of elements of gas ionization chamber 110 to provide sufficient area for placement of pins P1-P5.

As shown in FIG. 4, first electrode 211 includes region 230 containing holes, while similar regions containing holes are located in first dielectric layer 221, second dielectric layer 223, second electrode 215, and optional third dielectric layer 225 (third dielectric layer 225 may be present to shield second electrode 215 from ionization light, in order to reduce the production of photoelectrons due to the ionization light). As shown in FIG. 4, first dielectric layer 221 includes region 411 containing holes, second dielectric layer 223 includes region 413 containing holes, second electrode 215 includes region 415 containing holes, and third dielectric layer 225 includes region 417 containing holes. In an example embodiment, regions 411-417 may have an identical distribution of holes (i.e., corresponding holes in each region 411-417 may be positioned at the same lateral location within each region such that the holes of regions 411-417 are vertically aligned). In some embodiments, the vertically aligned holes of regions 411-417 may have the same size. Further, the holes in regions 411-417 may be vertically aligned, resulting in channels formed from the aligned holes.

As shown in FIG. 4, gas ionization chamber 110 may include a fence electrode 213, which is sandwiched between dielectric layers 221 and 223. In some embodiments, fence electrode 213 may include a large opening 421 aligned such that the entirety of regions 411 and 413 are correspondingly directly above and below opening 421. That is, opening 421 is arranged such that the holes of region 411 are vertically aligned with the holes of region 413 through opening 421. Further fence electrode 213 may have openings 422 and 423 for allowing respective conductive pins P2 and P4 to pass through these openings without touching fence electrode 213. In an example embodiment, while pin P2 is electrically connected to first electrode 211, pin P4 is configured to be electrically connected to second electrode 215. It is also contemplated that, in some embodiments, fence electrode 213 may include multiple openings (e.g., instead of large opening 421) arranged such these multiple holes together fluidly couple and vertically align the holes of the layer above (region 411) to the holes of the layer below (region 413).

In an example embodiment, pin P3 is configured to be electrically connected to fence electrode 213. Pin P1 is configured to pass through openings H1A-H1D (note that openings H1B and H1C are obscured by corresponding first dielectric layer 221 and fence electrode 213 and are shown by dashed lines, and opening H1D is partially obscured by second electrode 215 and is partially shown by dashed lines). Pin P2 is configured to pass through openings 441, H2A, 422, H2C, and H2D, pin P3 is configured to pass through openings H3A-H3D, pin P4 is configured to pass through openings H4A, 423, H4C, 442, and H4D, and pin P5 is configured to pass through openings H5A-H5D.

In various embodiments, first dielectric layer 221, fence electrode 213, second dielectric layer 223, and third dielectric layer 225 may have any suitable shape and may be sufficiently large to contain respective regions or openings 411, 421, 413, or 417. In an example embodiment, these elements of gas ionization chamber 110 may be circular. In an example embodiment, these elements may have the same area (i.e., size) and have their respective centers vertically aligned.

In various embodiments, holes 331A-331D, as shown in FIG. 3, may be suitably aligned to avoid any non-functional channels (i.e., channels that do not allow ionized gas to flow from first electrode 211 to second electrode 215). The multiple layers (e.g., electrode elements and dielectric layers) of ionization chamber 110 may be fabricated by any suitable method. Since these techniques are well known in the art, they are not described here. In some embodiments, one or more layers of the multiple layers of ionization chamber 110 may be fabricated separately and coupled together to form ionization chamber 110. For example, in some embodiments, first electrode 211, first dielectric layer 221, fence electrode 213, second dielectric layer 223, second electrode 215, and third dielectric layer 225 may be fabricated separately (using known fabrication techniques) and these layers coupled together as described above to form ionization chamber 110. In an example embodiment, first electrode 211 may be fabricated over a portion of the area of first dielectric layer 221. For example, first electrode 211 may be evaporated over first dielectric layer 221 or attached to first dielectric layer 221 using any other suitable techniques (e.g., using annealing, adhesion, etc.). In some cases, electrode 211 may be solidly attached to first dielectric layer 221, and in other cases, electrode 211 may not be solidly attached to first dielectric layer 221. Further, fence electrode 213 may be annealed or adhered to first dielectric layer 221 and/or second dielectric layer 222. Similar to electrode 211, fence electrode 213 may or may not be solidly attached to either one of first dielectric layer 221 or second dielectric layer 223. Additionally, second electrode 215 may be annealed or adhered to second dielectric layer 223 and/or third dielectric layer 225. Similar to electrode 211, second electrode 215 may or may not be solidly attached to either one of second dielectric layer 223 or third dielectric layer 225. As described above, dielectric material for various dielectric layers of gas ionization chamber 110 may be selected from a group of insulators with superior chemically inert characteristics such as polytetrafluoroethylene (PTFE) ceramic filled PTFE, as well as glass fiber filled PTFE. In an example embodiment, metallic electrodes (e.g., electrodes 211, 213, and 215) may be formed from copper (Cu), silver (Ag), gold (Au), or platinum (Pt). In an example embodiment, holes within elements of gas ionization chamber 110 may be formed using a PCB driller or a laser. In an example embodiment, third dielectric layer 225 may be a thin layer of a dielectric coating formed on sensing second electrode 215. Such dielectric coating may reduce the photoemission of electrons from second electrode 215.

As described above, pins P1-P5 may be formed from a conductive metal. In an example embodiment, pins P2 and P4 may be soldered to respective first electrode 211 and second electrode 215. In an example embodiment, pin P3 may be soldered to fence electrode 213. While five pins are shown, it should be noted that a larger or a fewer number of pins may be used. In an example embodiment, the number of pins should be no less than the number of functional conductive layers (i.e., electrodes 211, 213, and 215). Additionally, in order to firmly connect gas ionization chamber 110 to PCB 112, additional pins (e.g., pins P1 and P5) may be used.

While pins P2-P4 may be placed in any particular arrangement, a triangular arrangement 410, as indicated by lines shown in FIG. 4, may be used. Triangular arrangement 410 of the pins P2-P4 may result in a mechanically stable structure. Further, in some embodiments, pins P1 and P5 may be added to further mechanically strengthen the structure. In some cases, none of three pins out of five pins P1-P5 are configured to form a line. Thus, any of three pins out of five pins P1-P5 (e.g., P1, P2, and P3 pins) are configured to be placed in a triangular arrangement.

In various embodiments, thicknesses of electrodes 211, 213, 215 may range from several micrometers to hundreds of micrometers, and thicknesses of dielectric layers 221, 223, and 225 may range from a fraction of a millimeter to a few millimeters. For example, thicknesses of electrodes may be a few tens of micrometers (e.g., 30 micrometers, 40 micrometers, 50 micrometers, 60 micrometers, etc.), and thicknesses of dielectric layers may be a few tenths of a millimeter (e.g., 0.1 millimeters, 0.2 millimeters, 0.3 millimeters, 0.4 millimeters, 0.5 millimeters, etc.). In an example embodiment, an entire stack of layers 211, 221, 213, 223, 215, and 225 may have a thickness of about one to a few millimeters or less. In some cases, the thickness of the entire stack may be in a range of 0.7-2 millimeters.

In various embodiments, channels (e.g., channel 332A, as shown in FIG. 3) formed by aligned holes are configured to permit gas flow from the first electrode to the second electrode through an opening in the fence electrode, as described above. In an example embodiment, the aligned holes are arranged in a pattern having a central region with a first set of holes and a peripheral region having a second set of holes. For example, an arrangement of holes in region 230 is shown in FIG. 5. As described above, region 230 is a region containing holes in first electrode 211. Similar holes are formed in other layers, as described above, and are aligned underneath holes of region 230 to form channels penetrating all the elements of gas ionization chamber 110. FIG. 5 shows a top view of gas ionization chamber 110. As described above, first electrode 211 is electrically connected to Pin P2 and is placed directly above first dielectric layer 221. As shown in FIG. 5, second electrode 215 is connected to pin P4 and is located below second dielectric layer (as indicated by dashed line).

With reference to FIG. 5, central region 511 includes multiple holes 521 that will collectively be referred to as the first set of holes, and the peripheral region 513 includes multiple holes 523 that will collectively be referred to as the second set of holes. Further, for brevity, any hole from holes 521 is referred to as hole 521. Similarly, any hole from holes 523 is referred to as hole 523. It should be noted that, although the holes 521 and 523 are illustrated as circular holes, this is only exemplary. In general, these holes may have any shape. As illustrated in FIG. 5, in some embodiments, holes 521 may generally be smaller than holes 523. As shown in FIG. 5, holes 521 may have a first diameter $d_1$ that is less than a second diameter $d_2$ for holes 523. Although the dimension of the holes may depend upon the application, in some embodiments, the first diameter $d_1$ will be less than the second diameter $d_2$, $d_1$ may have a value less than or equal to about 0.5 millimeters (mm) or between about 0.1-0.5 millimeters, and $d_2$ may have a value between about 0.4-1.0 millimeters or greater than about 0.5 millimeters. In some cases, $d_2$ is selected to be less than a few millimeters. For example, in some embodiments, $d_1$ may be ≤about 0.5 mm and $d_2$ may be >0.5 mm. In some embodiments, all the holes 521 may have the same size (diameter, area, width, etc.), and all the holes 523 may have the same size. For example, all holes 521 may have a diameter less than or equal to about 0.5 millimeters, and all holes 523 may be greater than about 0.5 millimeters. In some embodiments, holes 521 and 523 may have the same size. In such embodiments, $d_1$ may be equal to $d_2$ and $d_1$ and $d_2$ may have any value. In some embodiments, $d_1 = d_2$ and $d_1$, $d_2$≤about 0.5 mm. For instance, hole diameters $d_1$ and $d_2$ may be 0.1 millimeters, 0.2 millimeters, 0.3 millimeters, 0.4 millimeters, 0.5 millimeters, etc. Alternatively, holes 521 (or holes 523) may have varying diameters throughout region 511 (or region 513). For example, the diameter of the holes may gradually decrease from the periphery to the center of the hole field.

In general, holes 521 may be smaller than holes 523 by any value. In an example embodiment, hole 521 may have a size (cross-sectional area, diameter, radius, width, etc.)

smaller than a corresponding size (cross-sectional area, diameter, radius, width, etc.) of hole 523. In some cases, the size of hole 521 may be smaller than the corresponding size of hole 523 by, for example, at least five percent. In some embodiments, the diameter (or cross-sectional area or width) of hole 521 may be smaller than the diameter (or cross-sectional area or width) of hole 523 by at least five percent. In general, the size of hole 521 may be smaller than the corresponding size of hole 523 by any value between about 5-50% (e.g., 5%, 10%, 20%, 25%, 30%, 40%, 50%, etc.).

In some embodiments, multiple holes 521 (e.g., all the holes) may have a size smaller than the corresponding size of at least one hole 523 of the second set of holes by any value between about 5-50% (e.g., 5%, 10%, 20%, 25%, 30%, 40%, 50%, etc.). In some embodiments, all the holes 521 may have a cross-sectional area smaller than the smallest cross-sectional area hole 523 of the second set of holes by at least five percent (or any value between about 5-50%). Alternatively, all the holes 521 may have a cross-sectional area smaller than the largest cross-sectional area of a hole 523 by at least five percent (or any value between about 5-50%).

Alternatively, all the holes 521 may have a diameter smaller than the diameter of at least one hole of holes 523 by at least five percent. Additionally, all the holes 521 may have a diameter smaller than the smallest diameter of a hole of holes 523 by at least five percent. Alternatively, all the holes 521 may have a diameter smaller than the largest diameter of a hole of holes 523 by at least five percent.

In an example embodiment, holes in region 230 have a circular shape. Alternatively, holes may have other shapes (e.g., rectangular, square, pentagon, hexagon, elliptical, etc.). In some cases, a shape may be selected to limit variations in the curvature of a boundary of the shape (e.g., shapes with sharp corners may not be selected). In some cases, a curvature may preferably be smaller than a target threshold. Additionally, or alternatively, a variation in curvature may be preferred to be smaller than a target threshold. In an example embodiment, a threshold for curvature may be in a range of one to a hundred inverse millimeters.

In an example embodiment, a diameter of a hole within region 230 may have either a first value or a second value larger than the first value by at least five percent. For example, diameter $d_2$ of holes in peripheral region 513 may be larger than diameter $d_1$ of holes in central region 511 by at least five percent.

In various embodiments, reducing diameters $d_1$ and/or $d_2$ for holes within region 230 may improve linearity. For example, holes with a diameter of about or less than about 0.5 mm may improve the linearity of detector 100. For example, the reduction of the diameter of holes from 0.6 mm to about 0.5 mm may significantly improve linearity.

In some cases, holes with varying diameters may be employed for improving the linearity of the measurements and for maintaining the strength of a measured signal. For example, hole diameters lower than about 0.5 mm in the central region with bigger holes in the peripheral region may result in improved linearity without sacrificing the signal strength. In some cases, holes in region 230 may be uniformly smaller than 0.5 mm or may gradually increase from a small size to a bigger size from a center of region 230 towards a boundary of region 230 (i.e., towards a peripheral region).

In an example embodiment, region 230 includes a central point 235, as shown in FIG. 2, and a diameter of a hole may have a first value if a center of the hole is located within the first distance from central point 235 and has a second value if the center of the hole is located beyond the first distance from central point 235.

It should be noted that partitioning region 230 into two regions, such as peripheral region 513 and central region 511, is only one possible embodiment. Alternatively, region 230 may be partitioned into three, four, five, or more concentric regions, each one of the concentric regions characterized by holes having a region-specific range of diameters (or other sizes, e.g., width.) In an example embodiment, for two neighboring concentric regions, diameters of holes in a concentric region closer to a center of region 230 are smaller or the same as the diameters of holes in a neighboring concentric region further away from the center of region 230.

Figure 6A:
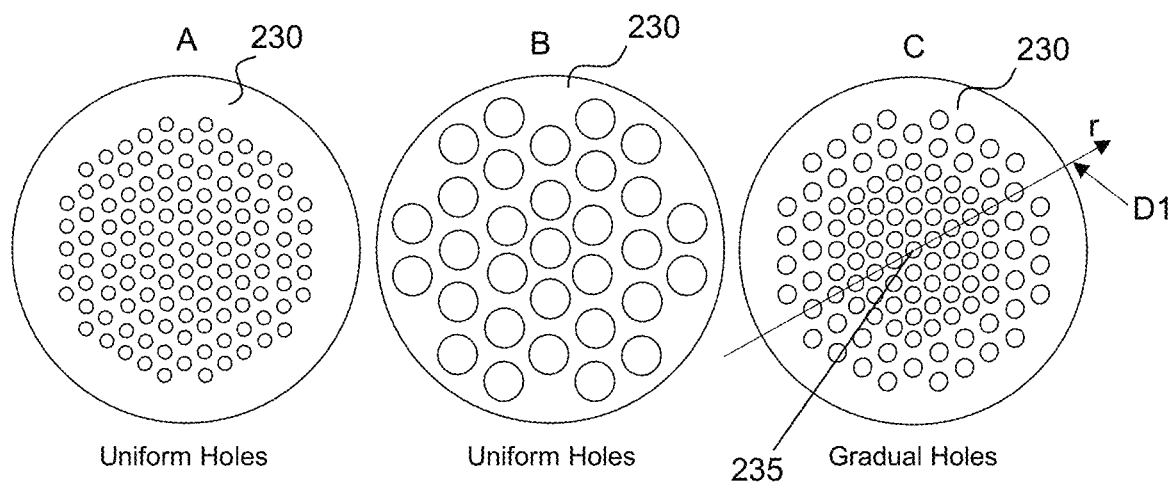
FIG. 6A is an example distribution of holes for a gas ionization chamber, consistent with disclosed embodiments.

FIG. 6A shows several examples of the distribution of holes within region 230. An example hole distribution A shows smaller holes of a diameter of a few tenths of a millimeter arranged in a hexagonal formation, an example hole distribution B shows larger holes (e.g., larger holes can be about one millimeter in diameter), and an example hole distribution C shows holes with smaller diameters at the center of region 230 and holes with larger diameters closer to a boundary of region 230. In an example embodiment, holes with a diameter less than a millimeter may be used.

Figure 6B:
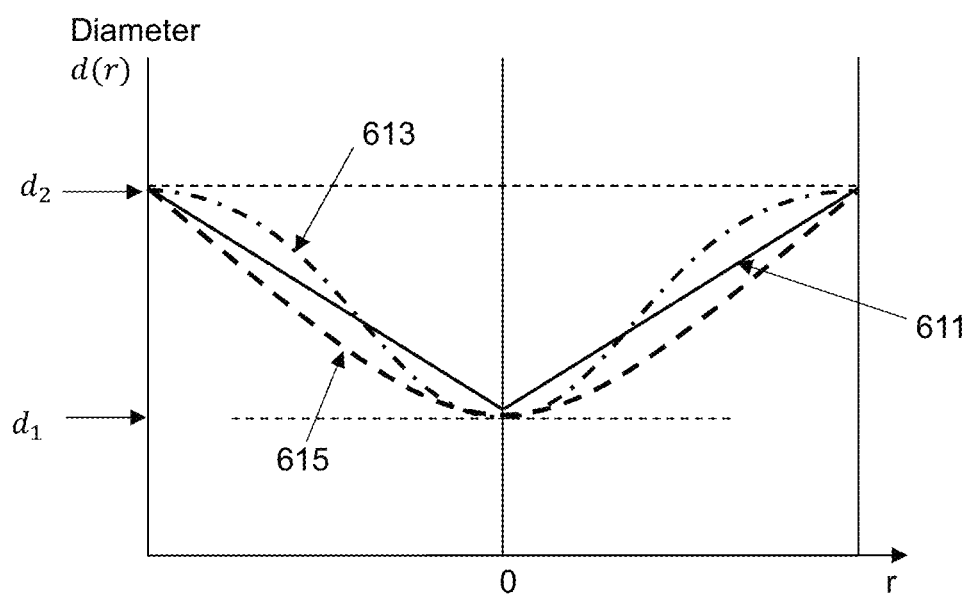
FIG. 6B are examples of graphs describing the distribution of holes for a gas ionization chamber, consistent with disclosed embodiments.

FIG. 6B shows an example distribution of hole diameters d(r) as a function of a distance r from a central point 235 (shown in FIG. 6A) of region 230. In an example embodiment, diameter d(r) may be a linear function of distance r as shown by graph 611. For such distribution of hole diameters, diameter d(r) for a hole in region 230 is proportional to a distance from the center of the hole to central point 235. The linear distribution of hole diameters d(r) is only one possible distribution. Alternatively, any other suitable distribution function may be used. For example, FIG. 6B shows graphs 613 and 615 that may be used as distributions of hole diameters d(r) as a function of distance r. In an alternative embodiment, an area of a hole in region 230 may be proportional to a distance from the center of the hole to central point 235.

Figure 6C:
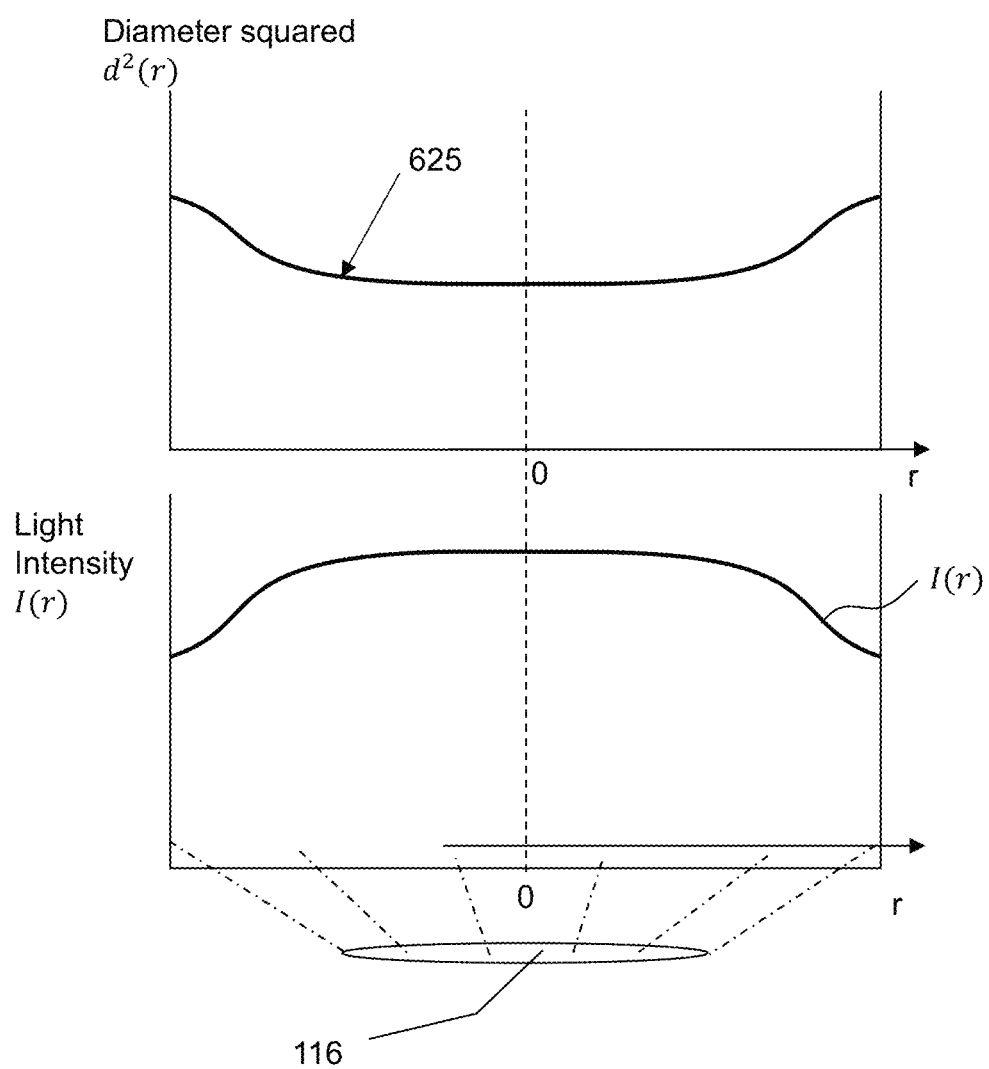
FIG. 6C is another example graph describing the distribution of holes for a gas ionization chamber, consistent with disclosed embodiments.

FIG. 6C shows an example hole distribution 625 of diameters $d^2(r)$ that may be selected based on the intensity of ionization light I(r) (herein, also referred to as the ionization radiation) from a light source 116. In an example embodiment, ionization light intensity I(r) may have a peak value at a lateral location close to central point 235, (i.e., I(0)=Max(I(r))) and may decrease as r increases. In an example embodiment $d^2(r)$ (or otherwise, areas of holes in region 230) may be inversely proportional to intensity I(r), as shown in FIG. 6C.

In another alternative embodiment, an area of holes in region 230 is selected such that a current measured due to ionized gas between first electrode 211 and second electrode 215 is substantially the same for each one of the channels formed due to the holes. For example, current due to ionized gas flowing through a channel formed by hole 521, as shown in FIG. 5, may be substantially the same as current due to ionized gas flowing through a channel formed by hole 523. Even though the diameter of hole 521 may be smaller than the diameter of hole 523, channels corresponding to these holes may carry the same current due to variations in the intensity of ionization light for holes 521 and 523. For example, if ionization light intensity for hole 521 is larger than for hole 523, a higher concentration of gas ions may be observed in the channel related to hole 521 than in the channel related to hole 523.

As shown in FIG. 6A, a large number of holes within region 230 may be used. In an example embodiment, a few holes, ten holes, a few tens of holes, fifty to a hundred holes, or more holes may be used. In some cases, region 230 may have an area of about one-half centimeter squared, one centimeter squared, two centimeters squared, etc. In an example embodiment, the diameter of the largest hole within region 230 may be less than 1 millimeter. For example, the diameter of the largest hole may be 0.1-0.9 millimeters.

Figure 7A:
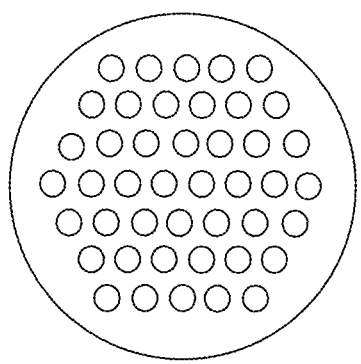
FIGS. 7A-7C show examples of arrangements of holes, consistent with disclosed embodiments.
Figure 7B:
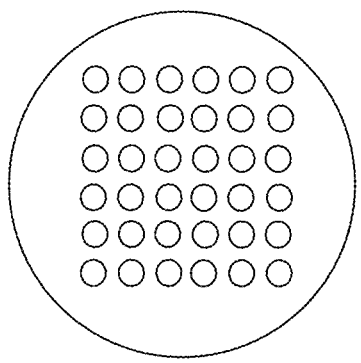
Figure 7C:
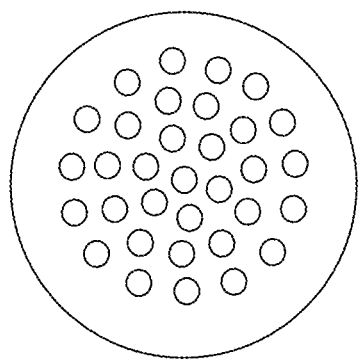

In various embodiments, holes within region 230 may be arranged using any suitable approach. For example, holes within region 230 may be arranged in a honeycomb (i.e., hexagonal) formation, as shown in FIG. 7A, a rectangular formation, as shown in FIG. 7B, a circular formation, as shown in FIG. 7C, or in any other suitable formation.

Figure 8A:
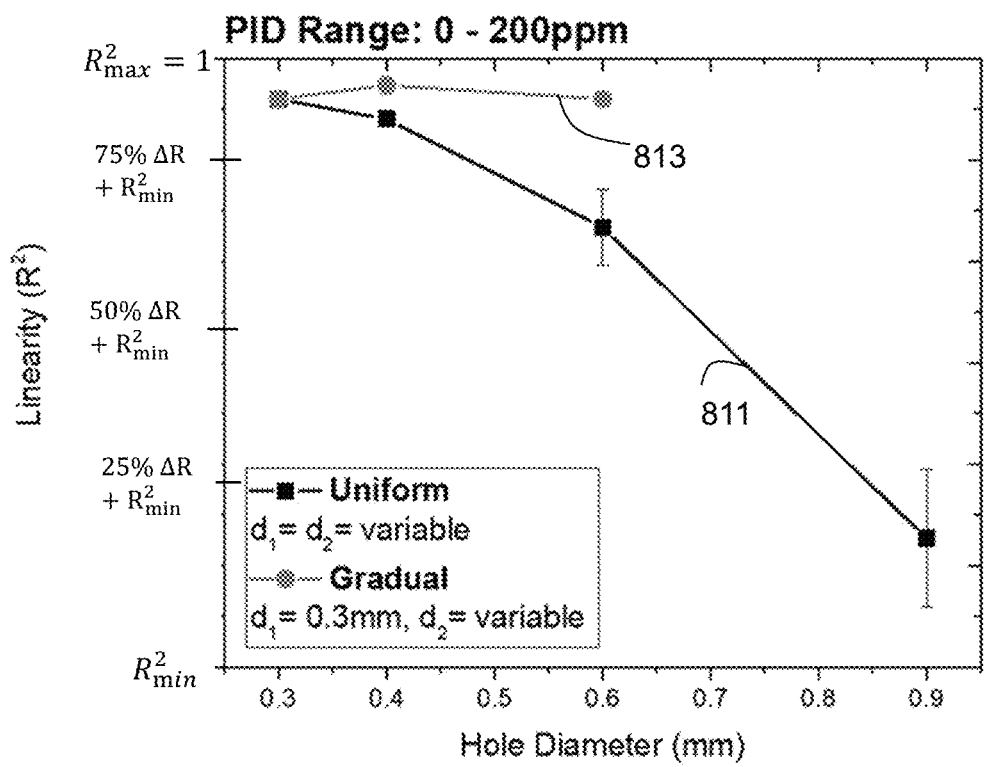
FIGS. 8A-8B show dependence of linearity of the device on the size and the distribution of holes, consistent with disclosed embodiments.
Figure 8A:
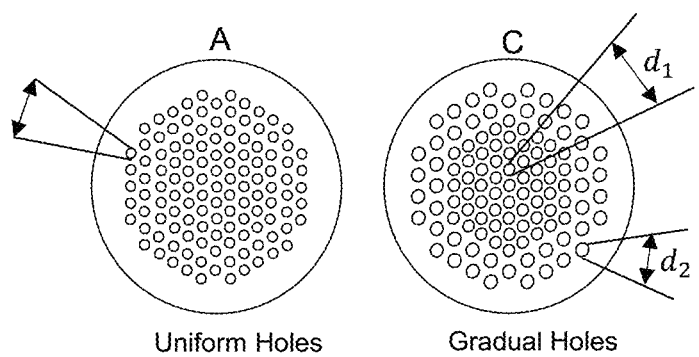
Figure 8B:
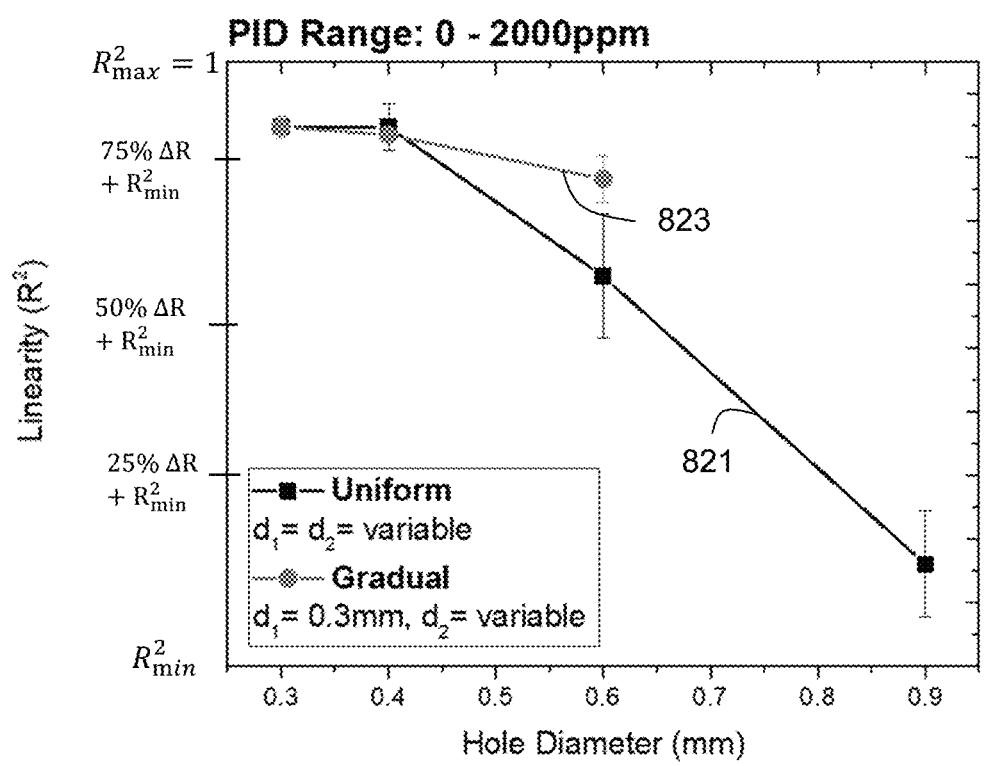
Figure 8B:
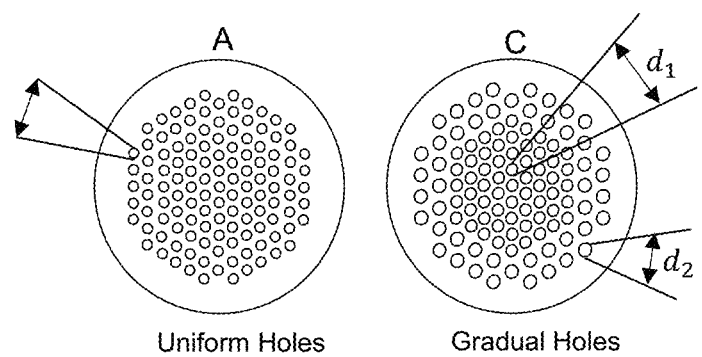

FIGS. 8A and 8B show plots of linearity of detector 100 as described by the coefficient of determination $R^2$. As known in statistics, $R^2$ determines a percentage variation in the dependent variable attributed to changes in the independent variable. In an example embodiment, $R^2=0.9$ indicates that 90% of data points fall on a regression line. Thus, high values of $R^2$ indicate a high correlation of a dependent variable with an independent variable. FIG. 8A shows the dependence of $R^2$ on size of holes for both cases when all the holes have the same diameter ($d_1=d_2$), as indicated by graph 811, and for cases when holes gradually increase from diameter $d_1$ to diameter $d_2$, as shown by graph 813. Linearity $R^2$ is shown to vary from a minimum value $R_{min}^2$ a maximum value $R_{max}^2=1$. A difference between $R_{max}^2$ and $R_{min}^2$ is indicated as $\Delta R = R_{max}^2 - R_{min}^2$. Graph 811 shows that when holes in region 230 are small (e.g., when the diameter of holes $d_1=d_2 \sim 0.3$-0.4 millimeters) $R^2$ is close to $R_{max}^2=1$. When hole diameter is increased larger than 0.4 millimeters, linearity $R^2$ is decreased. Graph 813 shows that when the diameter of holes is varied gradually from diameter $d_1=0.3$ millimeters to diameters $d_2=0.4$, or 0.6 millimeters linearity $R^2$ remains substantially constant and is close to $R_{max}^2=1$. FIG. 8A shows $R^2$ for signal resulted from TVOC with concentrations in a range of 0 to 200 parts per million (ppm). FIG. 8B shows similar graphs (graph 821 for uniform holes for which $d_1=d_2$ And graph 823 for gradually increasing holes with $d_1=0.3$ millimeters), but for TVOC concentrations in a much larger range of values of 0 to 2000 ppm. Similar to data of FIG. 8A, graph 821 shows that when holes in region 230 are small (e.g., when the diameter of holes $d_1=d_2 \sim 0.3$-0.4 millimeters) $R^2$ is close to $R_{max}^2=1$. Graph 823 shows that when the diameter of holes is varied gradually from diameter $d_1=0.3$ millimeters to diameters $d_2=0.4$, or 0.6 millimeters linearity $R^2$ remains substantially constant and is close to $R_{max}^2=1$.

In an example embodiment, a distance between two neighboring holes (the distance may be measured from a center of a first circular hole to a center of a second neighboring circular hole, and such distance herein is referred to as a center-to-center distance) may be larger than a diameter of the largest of the two neighboring holes by at least five percent. In some embodiments, the shortest distance between an edge of the first hole to an edge of the second neighboring hole (herein, referred to as an edge-to-edge distance) may be less than about one millimeter. In an example embodiment, the edge-to-edge distance between neighboring holes may be about a diameter of the smallest one or the largest one of the two neighboring holes. In some cases, the edge-to-edge distance between neighboring holes may vary throughout region 230. For example, the edge-to-edge distance between neighboring holes may increase as hole diameters are increasing within region 230. Alternatively, the edge-to-edge distance between neighboring holes may decrease as hole diameters are increasing. In some cases, the edge-to-edge distance between neighboring holes and diameters of neighboring holes are selected to result in a substantially constant current density (i.e., substantially constant current per unit area of region 230) due to the flow of ionized gas through channels formed by holes in region 230. In some cases, the edge-to-edge distance between neighboring holes may be in a range of 0.4-2 millimeters, and in other cases, the edge-to-edge distance between neighboring holes may be larger than 2 millimeters (e.g., 2-10 millimeters).

Figure 9A:
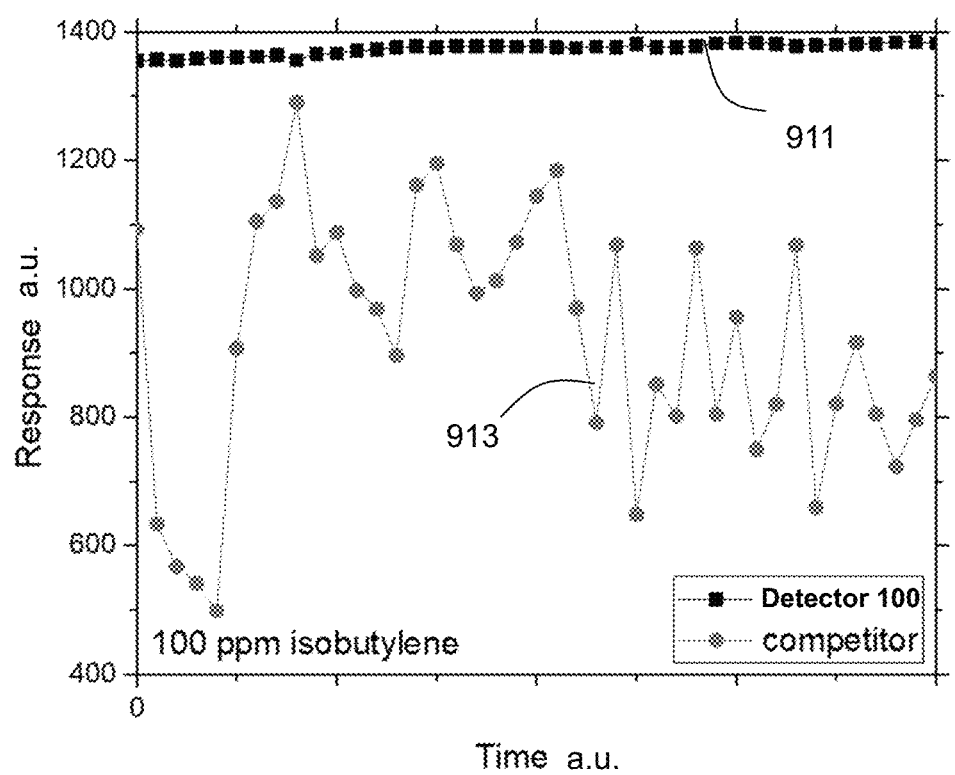
FIG. 9A-9B show example responses of a grounded photo-ionization detector, consistent with disclosed embodiments.
Figure 9B:
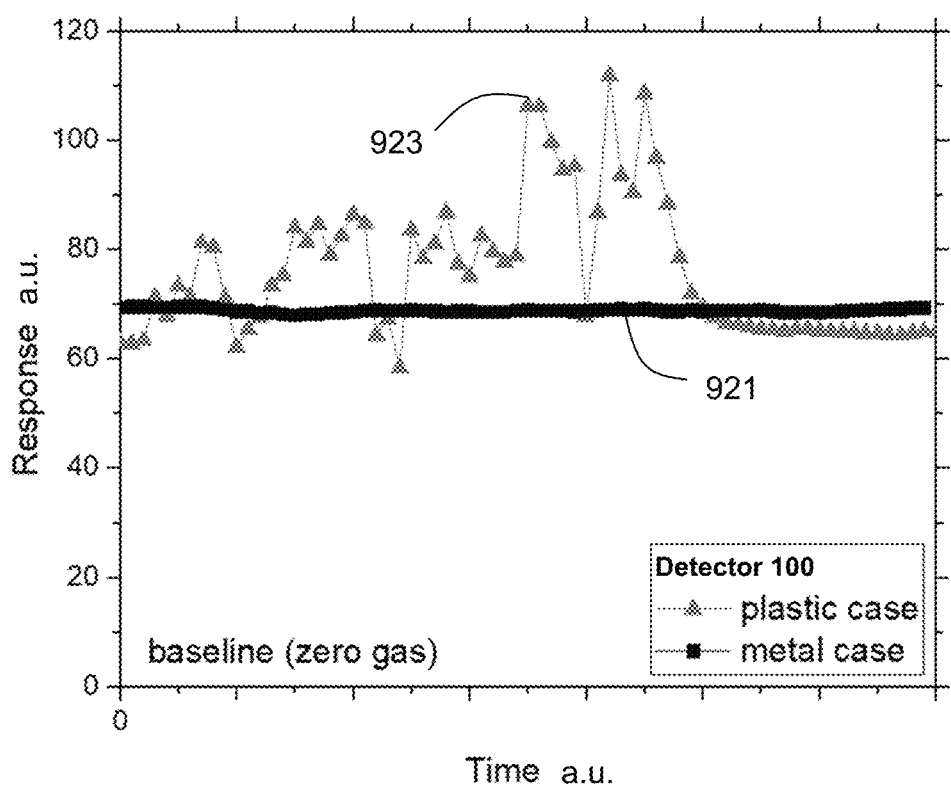

As previously described, detector 100 includes enclosure 101 that, in an example embodiment, is formed from a conductive material (e.g., a metal such as copper, aluminum, steel, etc.). In an example embodiment, enclosure 101 may be electrically connected to a ground potential level (i.e., grounded). Such grounded enclosure 101 may reduce signal noise due to external electromagnetic fields. In an example embodiment, both enclosure 101 and fence electrode 213 may be electrically connected to a ground potential level. FIGS. 9A and 9B show stability of a signal for grounded enclosure 101 of detector 100 when detector 100 is exposed to electromagnetic interference. As seen in FIG. 9A, graph 911 corresponds to a grounded detector 100 having grounded metal enclosure 101, and graph 913 corresponds to a detector without a grounded metal enclosure. Similarly, in FIG. 9B, graph 921 corresponds to a grounded detector 100 having grounded metal enclosure 101, and graph 923 corresponds to detector 100 having a plastic enclosure 101. FIGS. 9A and 9B show that grounded detector 100 with grounded metallic enclosure 101 provides for a stable signal (herein, referred to as a response) as compared to a signal from a detector that is not grounded. Compared to plastic enclosures, metallic enclosure 101 connected to the ground provides electromagnetic shielding and may significantly improve the sensor stability under strong electromagnetic interference (EMI).

In an example embodiment, metallic enclosure 101 may be sufficiently small (e.g., the largest dimension of enclosure 101 may be a few centimeters), portable, and compatible with general electrochemical sensors to allow detector 100 to be usable in both portable or stationary multi-sensor instruments.

The foregoing description has been presented for purposes of illustration. It is not exhaustive and is not limited to precise forms or embodiments disclosed. Modifications and adaptations of the embodiments will be apparent from a consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless otherwise noted, the relative terms, such as, for example, "in proximity," "close to," "about," "substantially the same," and the like, when comparing values implies that the values are at most ten percent different from each other.

As used herein, unless otherwise noted, the term "greater," "higher," "larger," "above," and the like, when comparing two values, the first value being greater than the second value, implies that the first value is at least one percent greater than the second value. Similarly, unless otherwise noted, the term "less," "lower," "smaller," and the like, when comparing two values, the first value being less than the second value, implies that the first value is at least one percent smaller than the second value. As used herein, unless otherwise noted, the term "comparable," "similar," and the like, when comparing two values, implies that one value is in the range of 10 to 100 percent of another value.

Further, as used herein, unless otherwise noted, the term "set" means one or more (i.e., at least one), and the phrase "any solution" means any now known or later developed solution.

Other embodiments will be apparent from a consideration of the specification and practice of the embodiments disclosed herein. It is intended that the specification and examples be considered as an example only, with a true scope and spirit of the disclosed embodiments being indicated by the following claims.

What is claimed is:

1. A gas ionization chamber, comprising:
   a set of stacked elements including:
      a first electrode;
      a fence electrode disposed below the first electrode;
      a second electrode disposed below the fence electrode;
      a first dielectric layer disposed between the first electrode and the fence electrode; and
      a second dielectric layer disposed between the fence electrode and the second electrode,
      wherein at least the first electrode, the second electrode, the first dielectric layer, and the second dielectric layer include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes, and
      wherein a diameter of at least one hole of the first set of aligned holes is less than or equal to about 0.5 millimeters.

2. The chamber of claim 1, wherein a diameter of each hole of the first set of aligned holes is less than or equal to about 0.5 millimeters.

3. The chamber of claim 2, wherein a diameter of each hole of the second set of aligned holes is less than or equal to about 0.5 millimeters.

4. The chamber of claim 2, wherein a diameter of a largest hole of the second set of aligned holes is greater than a diameter of a largest hole of the first set of aligned holes.

5. The chamber of claim 2, wherein a diameter of each hole of the second set of aligned holes is greater than a diameter of a largest hole of the first set of aligned holes.

6. The chamber of claim 1 further comprising:
   a first metallic pin electrically connected to the first electrode,
   a second metallic pin electrically connected to the fence electrode; and
   a third metallic pin electrically connected to the second electrode,
   wherein the first metallic pin, the second metallic pin, and the third metallic pin are arranged in a triangular formation.

7. The chamber of claim 6, further comprising at least one additional metallic pin electronically connected to the fence electrode.

8. The chamber of claim 1, wherein a distance between centers of neighboring holes in the first electrode, is larger than a diameter of a largest hole in the first electrode by at least five percent.

9. The chamber of claim 1, wherein a region containing holes in the first electrode includes a central point and wherein a diameter of a hole from the region containing the holes is proportional to a distance from a center of the hole to the central point.

10. The chamber of claim 1, wherein a shortest distance between edges of laterally neighboring aligned holes from the plurality of the aligned holes is less than about one millimeter.

11. A photo-ionization detector for testing gas, comprising:
    a gas ionization chamber having a set of stacked elements including:
       a first electrode;
       a fence electrode disposed below the first electrode;
       a second electrode disposed below the fence electrode;
       a first dielectric layer disposed between the first electrode and the fence electrode; and
       a second dielectric layer disposed between the fence electrode and the second electrode,
       wherein at least the first electrode, the second electrode, the first dielectric layer, and the second dielectric layer include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes,
       wherein a diameter of multiple holes of the first set of aligned holes is less than or equal to about 0.5 millimeters; and
    a set of electrically conductive pins including:
       a first electrically conductive pin electrically connected to the first electrode;
       a second electrically conductive pin electrically connected to the fence electrode; and a third electrically conductive pin electrically connected to the second electrode, wherein the first, second, and third electrically conductive pins are arranged in a triangular pattern;

an ionization light source positioned such that ionization light from the ionization light source is configured to pass through the plurality of the aligned holes for ionizing gas within the plurality of the aligned holes; and a circuit board electrically connected to both the ionization chamber and the ionization light source.

12. The detector of claim 11, further comprising:
a metallic enclosure having a top cap with a plurality of openings,
whereas the metallic enclosure houses the ionization chamber, the ionization light source, and the circuit board, and
whereas the plurality of openings allows the testing gas to pass through the ionization chamber.

13. The detector of claim 11, wherein a diameter of each hole of the first set of aligned holes is less than or equal to about 0.5 millimeters and a diameter of each hole of the second set of aligned holes is one of (a) less than or equal to about 0.5 millimeters or (b) greater than 0.5 millimeters.

14. The detector of claim 11, wherein diameters of the plurality of aligned holes decrease from the peripheral region to the central region.

15. The detector of claim 11, the gas ionization chamber further comprising:
a fourth pin passing through the set of the stacked elements; and
a fifth pin passing through the set of the stacked elements.

16. The detector of claim 11, wherein the multiple gas-flow channels include a first set of channels and a second set of channels, the first set and the second set of channels each including a plurality of gas-flow channels, wherein the plurality of gas-flow channels of the second set are arranged peripherally around the plurality of gas-flow channels of the first set, and wherein at least one gas-flow channel of the first set is smaller in a diameter than at least one gas-flow channel of the second set by about 5 to 50 percent.

17. The detector of claim 11, wherein a diameter of a largest hole of the first set of aligned holes is smaller than a diameter of a smallest hole of the second set of aligned holes.

18. A photo-ionization detector for testing gas, comprising:
a set of stacked elements including:
a first electrode;
a fence electrode disposed below the first electrode;
a second electrode disposed below the fence electrode;
a first dielectric layer disposed between the first electrode and the fence electrode; and
a second dielectric layer disposed between the fence electrode and the second electrode,
wherein at least the first electrode, the second electrode, the first dielectric layer, and the second dielectric layer include a plurality of aligned holes forming channels configured to permit gas flow between the first electrode to the second electrode through an opening in the fence electrode, the plurality of aligned holes being arranged in a pattern having a central region with a first set of aligned holes and a peripheral region having a second set of aligned holes,
wherein a diameter of each hole of the first set of aligned holes is less than or equal to about 0.5 millimeters and a diameter of each hole of the second set of aligned holes is one of (a) less than or equal to about 0.5 millimeters or (b) greater than 0.5 millimeters;
a first electrically conductive pin electrically connected to the first electrode;
a second electrically conductive pin electrically connected to the fence electrode;
a third electrically conductive pin electrically connected to the second electrode, wherein the first, second, and third electrically conductive pins are arranged in a triangular pattern;
fourth and fifth electrically conductive pins electrically connected to the fence electrode;
an ionization light source positioned such that ionization light from the ionization light source is configured to pass through the plurality of the aligned holes for ionizing gas within the plurality of the aligned holes,
a circuit board electrically connected with the stacked elements via the first, second, third, fourth, and fifth pins, and electrically connected with the ionization light source, and
a metallic enclosure with a top cap having a plurality of openings, wherein the metallic enclosure houses the ionization chamber, the ionization light source, and the circuit board, and wherein the plurality of openings allows the testing gas flowing through the ionization chamber.

19. The detector of claim 18, wherein the top cap of the metallic enclosure is configured to be removable.

20. The detector of claim 18, wherein the metallic enclosure is configured to be connected to a ground potential.

* * * * *

UNITED STATES PATENT AND TRADEMARK OFFICE
CERTIFICATE OF CORRECTION

PATENT NO. : 11,143,619 B1
APPLICATION NO. : 17/228287
DATED : October 12, 2021
INVENTOR(S) : Chen et al.

Page 1 of 1

It is certified that error appears in the above-identified patent and that said Letters Patent is hereby corrected as shown below:

On the Title Page

Item (57), Abstract, Line 1, "chamber, includes" should read as --chamber includes--.

In the Claims

Claim 8, Column 16, Line 27, "electrode, is" should read as --electrode is--.

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*